United States Patent [19]

Fischell

[11] Patent Number: 4,784,660
[45] Date of Patent: * Nov. 15, 1988

[54] MANUALLY ACTUATED HYDRAULIC SPHINCTER HAVING A MECHANICAL ACTUATOR

[75] Inventor: Robert E. Fischell, Silver Spring, Md.

[73] Assignee: The Johns Hopkins University, Baltimore, Md.

[*] Notice: The portion of the term of this patent subsequent to Feb. 25, 2003 has been disclaimed.

[21] Appl. No.: 831,950

[22] Filed: Feb. 24, 1986

Related U.S. Application Data

[63] Continuation-in-part of Ser. No. 421,441, Sep. 21, 1982, Pat. No. 4,571,749.

[51] Int. Cl.$^4$ .................... A61F 2/04; A61B 19/00
[52] U.S. Cl. .................... 623/14; 128/DIG. 25; 600/31
[58] Field of Search ............ 604/9, 8, 7; 128/1 R, 128/DIG. 25; 623/14

[56] References Cited

U.S. PATENT DOCUMENTS 3,553,967  1/1971  Porter et al. ............ 60/533
3,815,576  6/1974  Balaban ............ 128/DIG. 25
3,827,439  8/1974  Schulte et al. ............ 604/9
4,106,510  8/1978  Hakim et al. ............ 604/9
4,464,168  8/1984  Redmond et al. ............ 604/9
4,549,531 10/1985  Trick ............ 128/DIG. 25
4,551,128 11/1985  Hakim et al. ............ 604/9
4,557,722 12/1985  Harris ............ 604/9
4,571,749  2/1986  Fischell ............ 128/1 R Primary Examiner—Richard J. Apley
Assistant Examiner—David J. Isabella
Attorney, Agent, or Firm—Robert E. Archibald; Howard W. Califano

[57] ABSTRACT

An implantable hydraulic urinary sphincter system is disclosed for maintaining continence in those patients unable to control or stop inadvertent urinary flow. The invented apparatus generally consists of an artificial urinary sphincter and a control means for automatically increasing or decreasing sphincter pressure with sensed bladder and/or intra-abdominal pressure. An improved mechanical actuation means is also disclosed which allows the patient to urinate. To urinate the patient presses a push button centered on a septum located on the outer wall of the subcutaneously implanted control unit.

13 Claims, 2 Drawing Sheets

MANUALLY ACTUATED HYDRAULIC SPHINCTER HAVING A MECHANICAL ACTUATOR

CROSS-REFERENCE TO RELATED APPLICATION

This is a continuation-in-part of patent application Ser. No. 421,441, filed Sept. 21, 1982, now U.S. Pat. No. 4,571,749, and entitled "Manually Actuated Hydraulic Sphincter".

BACKGROUND OF THE INVENTION

1. Field of the Invention

The invention relates to an artificial sphincter for maintaining continence in those patients unable to control or stop inadvertent urinary flow. More particularly, the invention relates to a hydraulic sphincter which: automatically causes sphincter pressure to increase or decrease with sensed bladder pressure and/or intra-abdominal pressure; is manually actuated by the patient when he or she desires to urinate; and, allows sphincter fluid pressure to be measured and adjusted after implanation without necessitating a surgical procedure.

2. Description of the Prior Art

Urinary incontinence is a ubiquitous disorder which represents more than a personal inconvenience and social problem. For many, particularly those individuals suffering spinal injury, incontinence can cause life threatening complications. In the United States alone, it is estimated that 100,000 persons of all ages, many of them young veterans, have sustained spinal cord injuries rendering them incontinent. Pyelonephritis, a kidney infection produced by bacterial spread from the lower urinary tract, has been the leading cause of death among paralyzed World War II and Korean war veterans. Neurologic dysfunction of the urinary spincter can also occur because of multiple sclerosis, stroke, cerebrovascular disease, Parkinson disease and diabetes. Approximately 20% of the population over 65 suffer from incontinence. Women suffer "stress incontinence" largely the result of changes in bladder geometry following child birth. Many men experience incontinence after prostate surgery. Finally, incontinence can result from meningomyelocoele, amyotrophic lateral sclerosis, spinal cord or brain tumor, head injury, herniated disc, syringomyelia and tabes dorsalis.

Various attempts have been made to artificially produce urinary continence. Early attempts to prevent male incontinence involved externally clamping the penis; but, pressure sufficient to stop urinary flow tends also to compromise circulation, causing pain, skin alteration and thrombosis. An analogous application for women, compressing the urethra between the vaginal wall and the pubic bone, shares these disadvantages.

Several implantable artificial sphincters have, more recently, been disclosed in the prior art. U.S. Pat. No. 4,156,093 issued to Curtis Helms et al teaches the use of a fluid filled urethra collar which is contracted by manually squeezing a bulb implanted in the scrotum. In an article entitled "Implantation of an Artificial Sphincter for Urinary Incontinence" by F. B. Scott et al, in *Contemporary Surgery*, Vol. 18, Feb. 1981, results with such prior art artificial sphincters are reported. The article focuses on typical prior art devices which require a bulbous pump to be implanted in the scrotum of the male or in the labium of the female. In order to initiate urine flow the patient must compress the bulbous pump. The prior art devices are psychologically and cosmetically undesirable because of a general aversion most patients have to touching implants in such sensitive portions of the bodies as the scrotum and labium.

U.S. Pat. No, 3,815,576 issued to Donald R. Balaban teaches the use of a fluid filled flexible container implanted in the patient which is squeezed manually to actuate a piston-cylinder in a U-shaped clamp. Similarly, U.S. Pat. No. 4,056,095 issued to Pierre Rey et al and U.S. Pat. No. 4,0178,915 issued to Gerhard Szinicz et al teach the use of a fluid filled artificial sphincter which is actuated by pressing on the subcutaneously implanted membrane. These references share the disadvantage of having no control over the pressure exerted by the artificial sphincter on the urethra once the apparatus is implanted.

During the course of a research study (G. Timm et al), "Experimental Evaluation of an Implantable Externally Controllable Urinary Sphincter", *Investigative Urology* 11:326-330, 1974) it was found that artificial sphincter cuff pressure of 40 cm of $H_2O$ and above produce necrosis (tissue death) of the urethra. As a result, the prior art devices generally operate at a cuff pressure below 40 cm of $H_2O$. However, the normal bladder (and also the hypertrophic bladder), can produce high pressure transients, which result in dribbling incontinence for patients with these devices. U.S. Pat. No. 3,744,063 issued to McWhorter et al teaches controlling the flow of a fluid into the sphincter so that pressure applied to the urethra is graduated and controlled. However, variable pressure is controlled manually by applying digital pressure to an implanted pump chamber. Presumably, the patient increases the sphincter pressure after dribbling incontinence has occurred and been detected. The patient would not be able to respond to rapid changes in bladder pressure caused by bladder spasms, voluntarily or involuntary tensing of the diaphragm or abdominal wall, or increased intra-abdominal pressure due to walking, sitting, coughing or laughing.

The August 1981 issue of *Urology Times* contains an article reporting on an address by Dr. T. R. Malloy of the Pennsylvania Hospital in Philadelphia. Dr. Malloy has discovered that to reduce necrosis of the urethra it is necessary to have the artificial sphincter unfilled upon initial implant. It was found that urethra tissue swells immediately after surgery. If the artificial sphincter is filled it will exert an excessive pressure on the swollen urethra resulting in tissue necrosis. Dr. Malloy recommends allowing the swelling to decrease, followed by a second operation at a later time, merely to fill the sphincter chamber with fluid. The prior art artificial sphincters have no way of adding or replacing fluid in the artificial sphincter without surgery. Therefore, successful implantation of prior art devices require two separate surgical operations.

SUMMARY OF THE INVENTION

In copending U.S. patent application (Ser. No. 421,441, filed 9/21/82, now U.S. Pat. No. 4,571,749,), entitled "Manually Actuated Hydraulic Sphincter", which is incorporated herein by reference, Applicant disclosed a Manually Actuated Hydraulic sphincter (MAHS) which automatically increases sphincter pressure above a minimum pressure in accordance with sensed bladder and/or intra-abdominal pressure. The present patent application discusses many of the features previously disclosed in the above-referenced application plus new features which have been incorporated into the (MAHS) apparatus.

The apparatus generally consists of: a subcutaneously implanted control unit; an artificial sphincter that is hydraulically coupled to the control unit; and, a sensor bulb implanted at a selected site and also hydraulically coupled to the control unit. The implanted control unit includes a minimum pressure means for biasing fluid pressure in the artificial sphincter at an adjustable minimal or nominal fluid pressure. The implanted control unit also includes a pressure transfer means for adjusting fluid pressure in the artificial sphincter depending on pressure sensed by the pressure bulb; so that, the fluid filled artificial sphincter exerts just enough pressure on the urethra to prevent incontinence. The implantable control unit further includes an actuation means, manually controlled by applying pressure to an actuation button. The actuation means mechanically reduces the fluid pressure in the sphincter fluid chamber which in turn reduces the pressure exerted by the artificial sphincter on the urethra and thereby allows the patient to urinate.

Bladder pressure or abdominal pressure can increase rapidly because of bladder spasm, voluntary or involuntary tensing of the diaphragm or abdominal wall, or increased intra-abdominal pressure due to walking, sitting, coughing or laughing. If for example, the patient's bladder or diaphragm spasms, bladder pressure will increase rapidly. To prevent dribbling or stress incontinence the pressure exerted by the artificial sphincter on the urethra may be required to exceed diastolic pressure at least for that short period of time when the bladder pressure exceeds diastolic pressure. Prior art devices, to prevent such dribbling incontinence, would have to constantly maintain sphincter pressure above diastolic pressure thereby causing necrosis of urethral tissue which is permanently damaging. By contrast, the invented apparatus will automatically increase sphincter fluid pressure only for the length of the spasm, thereby causing no threat of tissue necrosis. The invented apparatus therefore can provide continence during bladder pressure peaks without causing necrosis of the urethral tissue. The pressure sensing bulb can be implanted in the wall of the bladder, thereby directly sensing bladder pressure, or it can be placed in the abdomen just below the bladder. When at the latter location, the pressure sensed would be that of abdominal pressure plus to some extent a pressure that is dependent on the extent to which the bladder is filled. Placement in the abdominal area may be advantageous if bladder wall surgery is difficult or contraindicated for a particular patient.

An additional advantage of the present invention is that the artificial sphincter can be implanted and remain void of fluid until the urethra has healed and swelling been reduced. The invention allows fluid to be added, after implantation, by inserting a hypodermic syringe through a septum into the invented device and adding fluid until an appropriate minimum sphincter pressure is obtained. The present invention can, therefore, be safely implanted without the need for the repeat operation required in the prior art. Furthermore, in the invented device, pressure exerted by the artificial sphincter can be measured and controlled at any time after implantation. For example, a low sphincter pressure can be initially set (e.g., 10 cm of H$_2$O above bladder pressure) which minimizes the possibility of urethral necrosis. If this pressure is shown to be insufficient to maintain continence, it can be increased using a simple hypodermic syringe that adds artificial sphincter fluid without requiring surgical intervention. If the minimum pressure required to maintain continence changes with time in a particular patient, it can be modified by adding fluid (to increase sphincter pressure) or removing fluid (to decrease sphincter pressure) by means of a hypodermic syringe. Any similar adjustment to prior art devices would have required an additional surgical operation.

To provide the above-stated advantages, the control unit contains two fluid filled chambers: a sphincter cuff fluid chamber, and a sensor pressure reference chamber. The sphincter cuff fluid chamber is hydraulically coupled to the artificial urethra sphincter cuff such that pressure exerted by the sphincter cuff varies according to the fluid pressure in the cuff chamber. The sensor pressure reference chamber is hydraulically coupled to the bladder pressure sensor bulb and fluid pressure in that chamber increases as the bladder pressure sensor bulb is compressed by increased bladder or intra-abdominal pressure. A common wall between the two chambers includes a resiliently biased member, such as a bellows. The fluid pressure in the artificial sphincter is adjusted to a minimum pressure determined by the spring rate of the bellows and the volume of fluid that is put into the sphincter cuff chamber.

A diaphragm/septum, included in the outer wall of the sphincter cuff chamber, allows entry of a hypodermic syringe into fluid communication with the cuff chamber. By increasing the fluid volume in the cuff chamber, the minimum pressure can be adjusted to a desired level. Therefore, the hypodermic syringe can inject or remove fluid from the sphincter fluid chamber thereby increasing or decreasing the minimum pressure.

As changes in the bladder or intra-abdominal pressure is sensed by the pressure sensing bulb, the resiliently biased member (bellows) located in the common wall cooperates with the pressure sensor reference chamber to form a pressure transfer means. As pressure increases or decreases in the sensor chamber, the pressure transfer means will cause a corresponding increase or decrease in the sphincter cuff pressure; so that, the fluid filled artificial sphincter cuff exerts just enough pressure on the urethra to prevent necrosis.

To allow the patient to urinate, a separator member is mechanically engaged as the patient presses on a push button through the skin and tissue. The push button is positioned in a diaphragm/septum located on the outer wall of the subcutaneously implanted control unit. As the separator member is mechanically engaged it presses on the bellows and decreases pressure in the cuff chamber, thus allowing the patient to urinate. This mechanical actuator represents an improvement to the hydraulic actuator described in the above-cited and copending Fischell patent application (entitled "Manually Actuated Hydraulic Sphincter"). The present improved (MAHS) apparatus only requires two fluid chambers, which represents a considerable simplification in design. The diaphragm function and the septum function are now combined into a single, thick, elastomer molded part which forms an outer wall of the sphincter fluid chamber. Also, the push button makes it easier for the patient to locate the exact center of the control unit under his skin, which is the ideal place on which to push in order to achieve the greatest volume removal from the cuff chamber with the least force.

The improved (MAHS) apparatus also uses a needle stop located within the sphincter fluid chamber at a position beneath the diaphragm/septum. This feature allows the adjustment of cuff pressure by adding or removing fluid via the hypodermic needle. The needle stop prevents the needle from exerting a force on the movable surface (bellows) of the sphincter cuff chamber; such force application would cause an erroneous pressure reading in the sphincter cuff chamber.

Still another advantage of the improved (MAHS) apparatus is the use of an elastomer band which encompasses the circumference of the control unit. The elastomer band satisfies the dual function of: (1) establishing a silicone rubber to silicone rubber interface between the band and the tubing connecting the control unit to the pressure sensor bulb and the sphincter cuff; and (2) providing suturing holes for attaching the control unit into the patient's body.

A first novel feature of the invention is a Manually Actuated Hydraulic Sphincter which can prevent incontinency, over a wide range of bladder and intra-abdominal pressure, without causing necrosis of the urethral tissue.

A second novel feature of the invention is the use of a control unit which automatically increases sphincter pressure in relation to increases in sensed bladder pressure and/or intra-abdominal pressure.

A third novel feature of the invention is the use of a control unit which has a pressure sensing bulb, implanted in association with the bladder, to sense bladder and/or intraabdominal pressure.

A fourth novel feature is the use of a control unit which contains a means for adjusting the minimum sphincter fluid pressure level after the unit is implanted.

A fifth novel feature is the use of a manual actuation means which is mechanically linked to push button located on the outer surface of the subcutaneously implanted control unit.

A sixth novel feature is the use of a control unit that can be adjusted after implantation to set or reset the sphincter fluid pressure.

A seventh novel feature is the ability to measure sphincter cuff pressure after implantation; and the use of a needle stop to prevent a hypodermic needle from applying pressure to the movable surface of the sphincter cuff chamber, which would cause an erroneous pressure reading.

An eighth novel feature is that the pressure sensing bulb is expanded each time the (MAHS) apparatus is actuated for voiding thus preventing the build-up of body tissue encapsulation around the sensing bulb.

A ninth novel feature is the use of a thick elastomer diaphragm/septum which serves the dual function of allowing a hypodermic needle into fluid access with the sphincter fluid chamber and also providing a flexible diaphragm for use in association with the push button mechanical actuation means.

A tenth novel feature is the use of a elastomer band for: (1) holding connecting tubes onto the control unit's body by establishing a silicone rubber to silicone rubber connection; and, (2) providing suturing holes for attaching the control unit at a preselected subcutaneous location.

DETAILED DESCRIPTION OF THE PREFERRED EMBODIMENT

Figure 1:
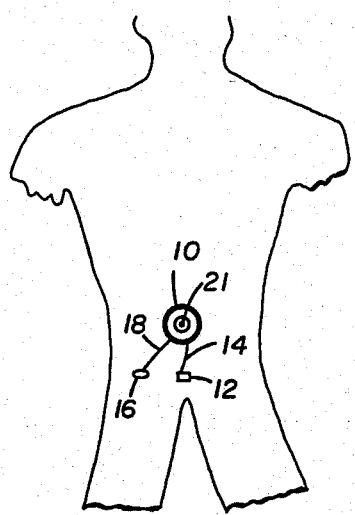
FIG. 1 illustrates the positioning of the various portions of the invented Manually Actuated Hydraulic Sphincter within a human body.

FIG. 1 shows the configuration of the (MAHS) apparatus within a human patient. A control unit is shown at 10 which is connected by fluid line 18 to a pressure sensing bulb 16. Also seen in FIG. 1 is a line 14 connecting the control unit 10 to an inflatable cuff 12 which surrounds the patient's urethra. The principle of operation of the MAHS device is that when finger pressure is exerted through the skin onto push button 21 of the control unit 10, the working fluid is removed from the inflatable cuff 12 and the patient can void. As soon as the finger pressure is removed from the push button 21, urinary continence is restored. The object of the pressure sensor 16 is to instantaneously increase the fluid pressure in the cuff 12 when sensed bladder pressure rises or when abdominal pressure rises suddenly, such as by coughing, so that stress incontinence is eliminated.

Figure 2:
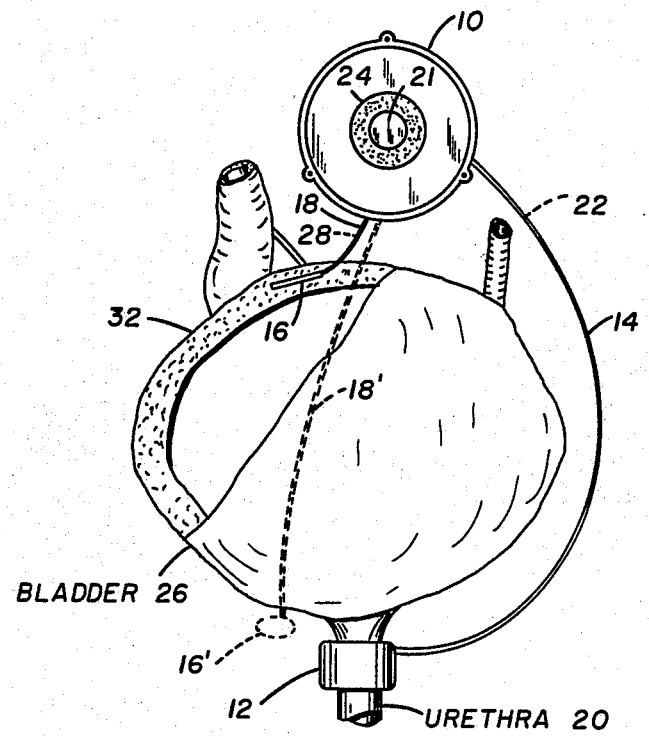
FIG. 2 is a diagrammatic view illustrating the orientation of various portions of the Manually Actuated Hydraulic sphincter relative to the bladder and urethra.

FIG. 2 shows a more detailed view of the invented apparatus as implanted in a patient. The artificial sphincter cuff 12 is shown surrounding a portion of the urethra 20. The artificial sphincter cuff 12 and associated pressure line 14 are filled with an incompressible sphincter fluid 22. As the pressure of the sphincter fluid 22 is increased or decreased by control unit 10, the pressure exerted by the cuff 12 on the urethra will correspondingly increase or decrease. The push button 21 is located on a thick elastomer diaphragm/septum 24 that forms part of the surface of control unit 10. When the control unit 10 is implanted subcutaneously, the push button 21 can be pressed by manually applying pressure to the skin just above the implant. As the patient presses and holds down the actuation push button 21, sphincter fluid pressure is reduced, enabling the patient to urinate. As soon as hand pressure is removed, the patient immediately becomes continent. A bladder pressure sensing bulb 16 is implanted in the wall 32 of the bladder 26 and senses bladder fluid pressure by compressing slightly as bladder pressure increases. Alternatively, the bladder pressure sensing bulb 16' can be placed anywhere in the abdomen, specifically in the abdomen just below the bladder. When at this location, the bulb can sense abdominal pressure plus to some extent a pressure which is dependent on bladder volume. The bladder pressure sensor bulb 16 (alternatively, bladder pressure sensing bulb 16') is filled with an incompressible reference pressure fluid 28, and is hydraulically linked by line 18 (alternatively, line 18') to control unit 10.

Figure 3:
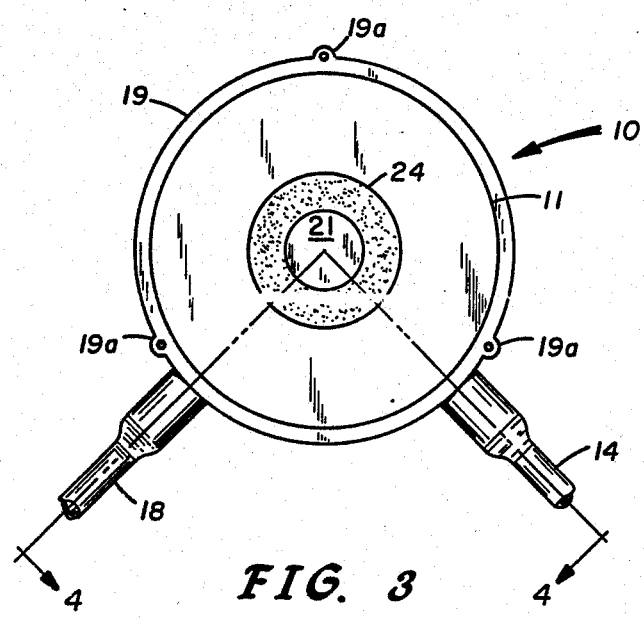
FIG. 3 is a top view of the control unit portion of the Manually Actuated Hydraulic Sphincter.

FIG. 3 is a more detailed top view of the improved control unit 10. The control unit has an upper shell 11 which is surrounded by an elastomer band 19 into which has been molded three suture holes 19a. The elastomer band 19 can be made from silicone rubber or other biocompatible elastomeric polymers. The purpose of the suture holes is to hold the implant in place immediately after surgery until fibrotic encapsulation occurs. The line 18 is connected to the sensor bulb 16 and the line 14 connects to the inflatable cuff 12. An important purpose of the band 19 is to join the lines 14 and 18 with a silicone rubber to silicone rubber connection which is much more secure than a silicone rubber to metal connection. This connection is typically bonded with silicone type adhesives. (Note: Although this feature has been described in connection with the MAHS apparatus, it is to be understood that it can be used in any environment in which a silicone rubber line is connected to the port of a metallic casing. For instance, any implantable device may contain a silicone rubber line which connects to a port of a metallic casing. Also, although lines 14 and 18, and elastomer band 19 have been described using silicone rubber, other biocompatible polymers could be substituted for the silicone rubber and provide the same advantage.)

Figure 4:
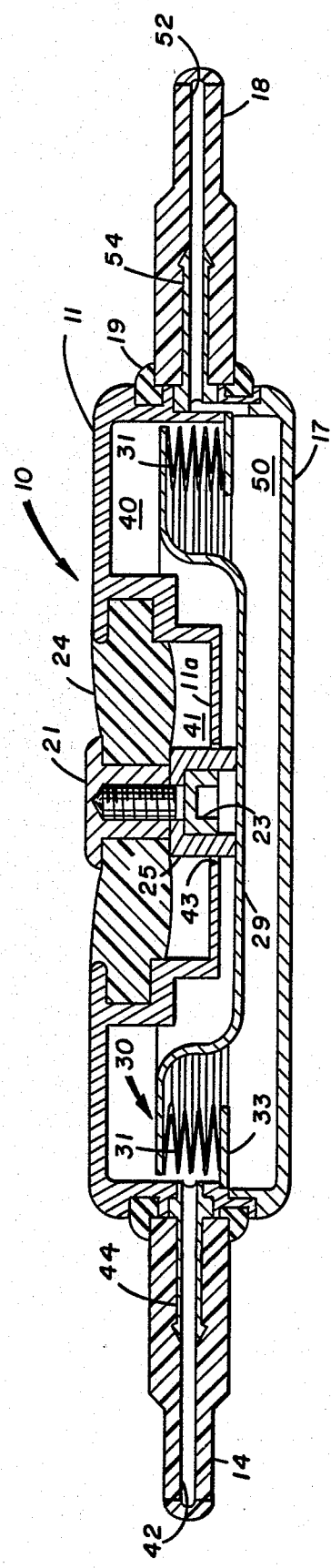
FIG. 4 is a cross-sectional view of the control unit with an improved mechanical actuation means.

FIG. 4 is a cross-sectional view of the actuator at 4—4 of FIG. 3. The elastomer diaphragm/septum 24 is centered within the upper shell 11. A push button 21 is held in place at the center of the diaphragm/septum 24 by means of a screw 23 which holds in place a separator 25. When finger pressure is applied through the skin onto the push button 21, the diaphragm/septum 24 is deflected downward and the separator 25 applies a downward force onto the bellows cover 29 of the bellows 30 thus causing a compression of the bellows convolutions 31. The annulus 33 is welded along its inner edge to the lowest of the bellows convolutions 31 and at its outer edge it is welded to the top shell 11. When the push button 21 is deflected downward causing the bellows cover 29 to be deflected downward, the cuff chamber 40 increases in volume which causes fluid to be sucked into the bellows chamber 40 from the cuff 12. The path of the cuff fluid is through the connecting tube 14 through the interior lumen 42 of the cuff port 44 and finally entering the cuff chamber 40. As previously described, when the push button 21 is deflected downward, the cuff chamber 40 fluid volume is increased resulting in fluid being withdrawn from the cuff 12 thus removing pressure from the patient's urethra and thereby allowing urination. When the pressure on the push button 21 is removed, the spring force of the convolutions 31 of the bellows 30 is such as to cause the cuff fluid to be pressurized at a predetermined adjustable minimum or nominal pressure which is set by the spring rate of the bellows 30 and the volume of fluid that is put into the cuff chamber 40. Continence is typically maintained by applying a fluid pressure to the cuff 12 between 20 and 80 cm of H2O.

Fluid can be added or removed from the cuff chamber 40 by placing a (typically) non-coring needle of a hypodermic syringe through the skin, through the diaphragm/septum 24 and finally entering the antechamber 41 which is in fluid communication with the cuff chamber 40 through the opening 43. A needle stop 11a prevents the hypodermic needle from applying force to the bellows cover 29 of the bellows 30 which force if applied could cause an error in the reading of the cuff chamber pressure. In this manner, the nominal pressure applied to the cuff 12 can be adjusted by the amount of fluid added to or removed from the cuff chamber 40. Once the cuff pressure adjustment has been made, the syringe with a (typically) non-coring hypodermic needle is pulled out of the diaphragm/septum 24 and out of the body.

The sensor bulb 16 is connected to the sensor chamber 50 of the control unit 10 by means of the connecting tubing 18 which connects to the interior lumen 52 of the sensor port 54 and finally into the sensor chamber 50. When increased pressure is applied to the sensor bulb 16, the pressure in the sensor chamber 50 is increased and this pressure is immediately transmitted through the cover 29 of the bellows 30 and causes an immediate increase in the pressure in the cuff chamber 40 and within the cuff 12. By this means, any sudden increase in pressure in the abdominal region caused by running, jumping, or coughing will immediately cause a comparable increase in the pressure exerted on the urethra by the cuff 12 thereby eliminating the possibility of stress incontinence. The sensor chamber 50 is enclosed on its bottom side by the bottom cover 17 which is welded along its periphery to the top cover 11.

Typical materials for such a device are silicone rubber for the diaphragm septum 24 and the outer ring 19; CP titanium or a titanium alloy can be used for all the metallic parts including the bellows convolutions 31; normal saline solution is typically used as the working fluid for both cuff fluid and sensor fluid. Silicone rubber, or other biocompatible elastomeric polymers, would be used for making the tubing 14, the tubing 18, the sensor bulb 16 and the urethral cuff 12.

To remove fluid from the cuff chamber 40 when pushing down on the push button 21, it is necessary that the area of the diaphragm/septum 24 in contact with the antechamber 41 be very much less than the area of the bellows cover 29. This is because downward deflection of the push button 21 causing downward deflection of the diaphragm/septum 24 results in increasing the pressure in the cuff chamber 40 while downward motion of the bellows cover 29 results in decreasing the pressure in the cuff chamber 40. Hence, to operate as intended, the area of the bellows cover 29 must be considerably greater than the area of the diaphragm/septum 24 that is in contact with the antechamber 41.

Obviously many modifications and variations of the present invention are possible in light of the above teaching. It is therefore to be understood that within the scope of the appended claims the invention may be practiced otherwise than as specifically described.

What is claimed and desired to be secured by Letters Patent of the United States is:

1. An implantable hydraulic urinary sphincter system comprising:
    an artificial sphincter means for exerting pressure on a patient's urethra;
    a control unit having a sphincter fluid chamber filled with incompressible sphincter fluid, said sphincter fluid chamber hydraulically coupled to said artificial sphincter means, and wherein pressure exerted by said artificial sphincter means varies according to said sphincter fluid pressure;
    a pressure sensor means for sensing pressure at a preselected location in a patient's body;
    a nominal pressure means for biasing sphincter fluid pressure to a selected nominal pressure, said nominal pressure means comprising a bellows;
    a pressure transfer means located within said control unit and associated with said pressure sensor means, for automatically adjusting sphincter fluid pressure depending on pressure sensed by said pressure sensor means; and,
    a mechanical actuation means associated with said control unit for mechanically actuating said bellows thereby decreasing the sphincter fluid pressure, wherein a decrease in sphincter fluid pressure decreases the pressure exerted by said artificial sphincter means.

2. The apparatus of claim 1, wherein a flexible septum forms at least a portion of an outer wall of said control unit and wherein the inner wall of said septum is in fluid communication with said sphincter fluid chamber.

3. The apparatus of claim 1, wherein said mechanical actuation means comprises:
   a septum forming a portion of an outer wall of said control unit; and,
   an actuator positioned on and extending through said septum and having a push button portion positioned on the external surface of said septum and a second portion extending internal to said control unit to a position proximate to said bellows, translational movement of said push button portion causes said second portion to transfer movement to said bellows.

4. The apparatus of claim 1, wherein said pressure sensor means further comprises a pressure sensor bulb filled with an incompressible fluid, and adapted to be implanted; and, wherein said pressure transfer means further comprises a pressure reference chamber, filled with incompressible reference fluid and hydraulically coupled to said pressure sensor bulb, said pressure reference chamber positioned in association with said sphincter fluid chamber such that said incompressible reference fluid is in fluid communication with one surface of said bellows, the sphincter fluid being in communication with the opposite surface of said bellows.

5. The apparatus of claim 2, further comprising a needle stop located within said control unit at a position proximate to said septum.

6. The apparatus of claim 1, wherein said artificial sphincter means and said pressure sensor means are hydraulically coupled to said control unit by lines, and wherein an elastomer band encompasses the circumference of said control unit, said elastomer band having at least two suturing holes and providing a compatible interface for adhering said lines in position relative to the surface of said control unit.

7. The apparatus of claim 3, wherein said septum is a thick elastomer septum.

8. The apparatus of claim 3, wherein said push button portion is centered on said septum.

9. An implantable hydraulic urinary sphincter system comprising:
   a control unit contained in a casing and adapted to be implanted subcutaneously comprising:
   a sphincter fluid chamber filled with an incompressible sphincter fluid, said sphincter fluid chamber mounted inside said casing, one wall of said sphincter fluid chamber containing a flexible septum positioned on the outer face of said casing, another wall of said sphincter fluid chamber includes a bellows, said bellows maintaining said sphincter fluid at a nominal pressure;
   a pressure reference chamber filled with an incompressible reference fluid and positioned inside said casing adjacent to said sphincter fluid chamber such that at least part of said bellows is a common wall to both said pressure reference chamber and said sphincter fluid chamber, increased fluid pressure in said pressure reference chamber causing said bellows to flex increasing the volume of said pressure reference chamber, decreasing the volume of said sphincter fluid chamber and increasing said sphincter fluid pressure;
   an actuator positioned on and extending through said septum and having a push button portion positioned on the external surface of said septum and a second portion extending internal to said control unit to a position proximate to said bellows, translational movement of said button portion causes said second portion to transfer movement to said bellows, thereby decreasing said sphincter fluid pressure;
   an artificial sphincter operably connected by a line to said sphincter fluid chamber, said artificial sphincter chamber being pressurized by said sphincter fluid; and,
   a pressure sensor bulb, connected by a flexible line to said pressure reference chamber, for varying the fluid pressure in said pressure reference chamber, as sensed pressure varies.

10. The apparatus of claim 9, further comprising a needle stop located within said sphincter fluid chamber at a position beneath said septum, so that a hypodermic needle inserted through said septum will be prevented from contacting said bellows.

11. The apparatus of claim 9, further comprising an elastomer band encompassing the circumference of said casing, said elastomer band having at least two suturing holes and providing a compatible interface for adhering said lines in position relative to the surface of said casing.

12. The apparatus of claim 9, wherein said septum is a thick elastomer septum.

13. The apparatus of claim 9, wherein said push button portion is centered on said septum.

* * * * *